(12) United States Patent
Friedman et al.

(10) Patent No.: US 9,877,713 B2
(45) Date of Patent: Jan. 30, 2018

(54) TENDON REPAIR APPARATUS

(71) Applicants: Guy Friedman, Ashkelon (IL); Hagar Patish, Ganei-Yehuda (IL); Yossi Suzer, Rishon-LeZion (IL)

(72) Inventors: Guy Friedman, Ashkelon (IL); Hagar Patish, Ganei-Yehuda (IL); Yossi Suzer, Rishon-LeZion (IL)

( * ) Notice: Subject to any disclaimer, the term of this patent is extended or adjusted under 35 U.S.C. 154(b) by 0 days.

(21) Appl. No.: 14/053,757

(22) Filed: Oct. 15, 2013

(65) Prior Publication Data

US 2014/0114351 A1    Apr. 24, 2014

Related U.S. Application Data (60) Provisional application No. 61/713,689, filed on Oct. 15, 2012.

(51) Int. Cl.
*A61B 17/08* (2006.01)
*A61B 17/04* (2006.01)
(Continued)

(52) U.S. Cl.
CPC ............ *A61B 17/04* (2013.01); *A61B 17/064* (2013.01); *A61B 17/1146* (2013.01);
(Continued)

(58) Field of Classification Search
CPC ... A61B 17/04; A61B 17/064; A61B 17/0643; A61B 17/0644; A61B 17/0647; A61B 17/068; A61B 17/072; A61B 17/07207; A61B 2017/0647; A61B 2017/0648; A61B 2017/0649; A61B 2017/1132; A61B 2017/1146; A61B 17/11; A61B 17/1114; A61B 17/1128; A61B 17/146; A61B 17/115; A61B 11/1152; A61B 17/1155; A61B 17/12; A61B 2017/1103; A61B 2017/1107; A61B 2017/111;
(Continued)

(56) References Cited

U.S. PATENT DOCUMENTS

| | | | |
|---|---|---|---|
| 4,738,062 A | 4/1988 | Dickey | |
| 5,591,206 A * | 1/1997 | Moufarrege | 606/215 |

(Continued)

FOREIGN PATENT DOCUMENTS

| | | |
|---|---|---|
| EP | 1221909 | 7/2002 |
| WO | WO 01/76488 | 10/2001 |
| WO | WO 2015/159277 | 10/2015 |

OTHER PUBLICATIONS

Crimp. Definition for English-Language Learners from Merriam-Webster's Learner's Dictionary. Retrieved Feb. 11, 2016 from http://learnersdictionary.com/definition/crimp.*

(Continued)

*Primary Examiner* — David C Eastwood
*Assistant Examiner* — Kankindi Rwego (57) ABSTRACT

An apparatus configured for coupling two portions of tissue of a subject, such as two portions of a transected tendon. In some embodiments, the apparatus comprises a first and second helical element and a locking element. Each helical element is configured to be coupled to a portion of tissue, and the locking element is configured to couple the first helical element to the second helical element such that the helical elements are collinear.

24 Claims, 6 Drawing Sheets

(51) Int. Cl.
*A61B 17/064* (2006.01)
*A61B 17/11* (2006.01)

(52) U.S. Cl.
CPC ... *A61B 17/0643* (2013.01); *A61B 2017/0647* (2013.01); *A61B 2017/0649* (2013.01); *A61B 2017/1132* (2013.01)

(58) Field of Classification Search
CPC ..... A61B 2017/1117; A61B 2017/1121; A61B 2017/1125; A61B 2017/1135; A61B 2017/1142; A61B 2017/1157
USPC .......................................................... 606/219
See application file for complete search history.

(56) References Cited

U.S. PATENT DOCUMENTS

| | | | |
|---|---|---|---|
| 5,810,851 A * | 9/1998 | Yoon | A61B 17/06 606/139 |
| 6,663,633 B1 * | 12/2003 | Pierson, III | A61B 17/0469 606/148 |
| 6,712,830 B2 | 3/2004 | Esplin | |
| 6,984,241 B2 * | 1/2006 | Lubbers | A61B 17/0401 606/103 |
| 7,959,648 B2 * | 6/2011 | Mas | A61B 17/0057 606/216 |
| 8,062,363 B2 | 11/2011 | Hirpara et al. | |
| 2007/0038221 A1 | 2/2007 | Fine et al. | |
| 2007/0225737 A1 | 9/2007 | Messerly et al. | |
| 2008/0082130 A1 | 4/2008 | Ward | |
| 2008/0108989 A1 | 5/2008 | Parsell et al. | |
| 2009/0069822 A1 * | 3/2009 | Takahashi | A61B 17/064 606/139 |
| 2009/0216252 A1 | 8/2009 | Melvin et al. | |
| 2011/0009902 A1 | 1/2011 | Leung et al. | |
| 2012/0330327 A1 | 12/2012 | McClellan | |
| 2017/0027578 A1 | 2/2017 | Friedman et al. | |

OTHER PUBLICATIONS

International Preliminary Report on Patentability dated Oct. 27, 2016 From the International Bureau of WIPO Re. Application No. PCT/IL2014/050361.

International Search Report and the Written Opinion dated Jan. 14, 2015 From the International Searching Authority Re. Application No. PCT/IL2014/050361.

Invitation to Pay Additional Fees dated Nov. 13, 2014 From the International Searching Authority Re. Application No. PCT/IL2014/050361.

* cited by examiner

TENDON REPAIR APPARATUS

RELATED APPLICATION

This application claims the benefit of priority under 35 USC § 119(e) of U.S. Provisional Patent Application No. 61/713,689 filed Oct. 15, 2012, the contents of which are incorporated herein by reference in their entirety.

FIELD OF THE INVENTION

Applications of the present invention relate generally to tissue repair, and specifically to implantable medical devices for facilitating tendon repair.

BACKGROUND

Tendon rupture is painful, and causes reduction or loss of movement in an affected joint. Typically, a ruptured tendon is repaired surgically, using sutures, in either an open or a percutaneous procedure. Alternatively, the tendon is not repaired surgically. Tendon rupture is typically more prevalent in males.

SUMMARY OF THE INVENTION

Apparatus is provided that comprises two helical elements, configured to be coupled to respective portions of at least one tissue, and to subsequently be coupled to each other, thereby coupling together the two portions of the tissue. Typically, the helical elements are configured to be lockably coupled to each other. Typically, the helical elements are configured to be coupled to exposed ends of a transected tendon by being screwed into the exposed ends, and the apparatus is configured to facilitate repair of the tendon.

There is therefore provided, in accordance with an application of the present invention, apparatus for use with at least one tissue of a subject, the apparatus including:

a first helical element, configured to be coupled to a first portion of the tissue of the subject;

a second helical element, configured to be coupled to a second portion of the tissue of the subject; and a locking element, configured, following the coupling of the first and second helical elements to the first and second portions of the tissue, to couple the first helical element to the second helical element such that the first and second helical elements are collinear.

In an application, the locking element is configured to lockably couple the first helical element to the second helical element.

In an application, no portion of the locking element includes suture.

In an application, the locking element includes suture.

In an application, the two helical elements are shaped to have the same handedness.

In an application, the apparatus is configured to inhibit an increase in a distance between the first and second portions of the tissue when (1) the first helical element is coupled to the first portion of the tissue, and (2) the second helical element is coupled to the second portion of the tissue and is lockably coupled by the locking element to the first helical element.

In an application:
the first portion of the tissue of the subject includes a first portion of a damaged tissue of the subject,
the second portion of the tissue of the subject includes a second portion of the damaged tissue of the subject, and
the apparatus is configured to facilitate repair of the damaged tissue of the subject.

In an application:
the damaged tissue includes a transected blood vessel of the subject, and
the apparatus is configured to facilitate repair of the transected blood vessel by being configured to inhibit an increase in a distance between first and second portions of the transected blood vessel.

In an application:
the damaged tissue includes a transected ureter of the subject, and
the apparatus is configured to facilitate repair of the transected ureter by being configured to inhibit an increase in a distance between first and second portions of the transected ureter.

In an application:
the damaged tissue includes a transected urethra of the subject, and
the apparatus is configured to facilitate repair of the transected urethra by being configured to inhibit an increase in a distance between first and second portions of the transected urethra.

In an application:
the damaged tissue includes a transected tendon of the subject, and
the apparatus is configured to facilitate repair of the transected tendon by being configured to inhibit an increase in a distance between first and second portions of the transected tendon.

In an application, the helical elements are configured to be screwed into respective exposed ends of the first and second portions of the transected tendon.

In an application, the helical elements are configured to not penetrate an epitenon of the tendon of the subject.

In an application:
each helical element has a distal end and a proximal end,
the distal end of each helical element is configured to be coupled to the tissue of the subject, and
the locking element includes two parts, each part of the locking element being coupled to a proximal end of a respective helical element, and the parts of the locking element being lockably couplable to each other.

In an application, one part of the locking element is shaped to define at least one slot, and the other part of the locking element is shaped to define at least one respective tab, the parts of the locking element being couplable to each other by the at least one tab being disposed in the at least one slot.

In an application, the distal end of each helical element is configured to penetrate the tissue of the subject.

In an application, the distal end of each helical element is shaped to define a cutting edge.

In an application, the distal end of each helical element is shaped to define a cutting edge that is asymmetrically tapered.

There is further provided, in accordance with an application of the present invention, a method for use with at least one tissue of a subject, the method including:

coupling a first helical element to a first portion of the tissue of the subject;

coupling a second helical element to a second portion of the tissue of the subject; and subsequently, lockably coupling the first helical element to the second helical element such that the first and second helical elements are collinear.

In an application, the method further includes, subsequent to coupling the helical elements to the portions of the tissue of the subject, and prior to coupling the first helical element to the second helical element, reducing a distance between the first and second portions of the tissue of the subject.

In an application, coupling the first helical element to the second helical element includes locking the first helical element to the second helical element.

In an application, coupling the first helical element to the second helical element does not include using suture.

In an application, coupling the first helical element to the second helical element includes inhibiting an increase in a distance between the first and second portions of the tissue.

In an application, coupling the first helical element to the second helical element includes coupling a first part of a locking element that is coupled to the first helical element, to a second part of the locking element that is coupled to the second helical element.

In an application, the locking element includes one or more tabs and one or more slots, and coupling the first part of the locking element to the second part of the locking element includes moving at least one of the tabs into at least one of the slots.

In an application, the at least one tissue includes a damaged tissue of the subject, and coupling the first and second helical elements to the first and second portions of the tissue includes coupling the first and second helical elements to first and second portions of the damaged tissue.

In an application, the method includes facilitating repair of the damaged tissue.

In an application, the first and second portions of the tissue include respective first and second portions of a transected blood vessel of the subject, and coupling the first and second helical elements includes coupling the first and second helical elements to the first and second portions of the transected blood vessel of the subject.

In an application, the first and second portions of the tissue include respective first and second portions of a transected ureter of the subject, and coupling the first and second helical elements includes coupling the first and second helical elements to the first and second portions of the transected ureter of the subject.

In an application, the first and second portions of the tissue include respective first and second portions of a transected urethra of the subject, and coupling the first and second helical elements includes coupling the first and second helical elements to the first and second portions of the transected urethra of the subject.

In an application, the first and second portions of the tissue include respective first and second portions of a transected tendon of the subject, and coupling the first and second helical elements includes coupling the first and second helical elements to the first and second portions of the transected tendon of the subject.

In an application, coupling the first and second helical elements to the first and second portions of the transected tendon includes screwing each helical element into a respective exposed end of a respective portion of the transected tendon.

In an application, coupling the first and second helical elements to the first and second portions of the transected tendon includes first and second helical elements to the first and second portions of the transected tendon without penetrating an epitenon of the tendon of the subject.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF EMBODIMENTS

Reference is made to FIGS. 1A-D and 2A-D, which are schematic illustrations of apparatus 20, comprising a first helical element 22 and a second helical element 24 that is couplable to the first helical element, in accordance with some applications of the invention. Apparatus 20 is not labeled in FIGS. 1A-D or 2A-D because, in these figures, helical elements 22 and 24 are not shown together. Apparatus 20 is labeled in FIGS. 3C and 4A-B. FIGS. 1A-D show helical element 22, and FIGS. 2A-D show helical element 24.

Helical elements 22 and 24 are configured to be coupled to respective portions of tissue of a subject, and to be lockably coupled to each other. Typically, apparatus 20 is configured such that helical elements 22 and 24 are couplable to each other after the helical elements are coupled to the respective portions of tissue. Apparatus 20 is thereby configured to hold together the respective portions of tissue of the subject (i.e., to inhibit an increase in a distance between the portions of tissue). Apparatus 20 is typically configured, and used, to facilitate repair of a transected (e.g., torn or cut) tendon of a subject, as described hereinbelow, e.g., with reference to FIGS. 3A-C. Alternatively, apparatus 20 may be configured to facilitate repair of other tissues (e.g., other elongate tissues, such as a blood vessel, ureter, or urethra of the subject).

Helical elements 22 and 24 each comprise a shaft 32 and 34, respectively, which are shaped to define respective helices. Typically, each helix has a transverse cross-sectional diameter of more than 0.2 mm and/or less than 10 mm (e.g., 0.5 mm-5 mm, such as 1 mm-5 mm), and a length of more than 0.5 cm and/or less than 3 cm (e.g., 0.5 cm-2 cm, such as 0.5 cm-1.5 cm). That is, helical elements 22 and 24 typically have (1) respective diameters d1 and d2 of more than 0.2 mm and/or less than 10 mm, and (2) respective lengths d3 and d4 of more than 0.5 cm and/or less than 3 cm.

Typically, the shafts comprise a metal such as, but not limited to, stainless steel, titanium, nickel titanium (Nitinol), nickel cobalt, and/or cobalt chrome. For some applications, the shafts comprise a polymer and/or a resin. Shafts 32 and 34 have respective cross-sectional diameters (e.g., bores) d5 and d6, which may be dimensioned according to specific applications, e.g., according to the tissue being repaired. Similarly, the pitch of the helix of the shafts may be configured according to specific applications.

Shafts 32 and 34 each have a distal end 42 and 44, respectively, configured to be coupled to the tissue (e.g., the tendon) of the subject, typically by being configured to penetrate, and to be screwed into, the tissue. For example, distal ends 42 and 44 may be shaped to define respective cutting edges 43 and 45. Typically, the cutting edges are asymmetrically tapered (e.g., generally chisel-shaped, such as in an atraumatic needle, as is known in the art). For example, the cutting edge may be formed by cutting and/or grinding the shaft from one side of the shaft only. For some applications, and as shown, the taper of the cutting edge of each helical element is on the inside of the helix formed by the shaft, such that the distal-most point of the cutting edge (e.g., the distal end of the shaft) is on the outside of the helix. Alternatively, the taper may be on the outside of the helix.

Typically, the helix defined by shaft 32 of element 22, and the helix defined by shaft 34 of element 24, have the same handedness. That is, helical element 22 and helical element 24 typically have the same handedness.

Typically, helical elements 22 and 24 comprise, or are shaped to define, one or more projections 26 (e.g., flanges), that are configured to generally allow the helical element to enter the tissue (e.g., when it is screwed into the tissue, as described hereinbelow, such as with reference to FIGS. 3A-C), but to inhibit movement of the helical element in the reverse direction (e.g., to inhibit inadvertent movement of the helical element out of the tissue). Typically, projections 26 are configured to flatten against the shaft of the helical element when the helical element is moved (e.g., screwed) into the tissue. For some applications, the shaft and projections comprise a continuous piece of material (e.g., projections 26 are formed, such as cut and/or splintered, from the shaft). For some applications, the projections comprise discrete pieces of material and are coupled to the shaft.

Typically, apparatus 20 further comprises a locking element 50, comprising a first part 52, coupled to helical element 22, and a second part 54, coupled to helical element 24. Locking element 50 is not labeled in FIGS. 1A-D or 2A-D because, in these figures, parts 52 and 54 are not shown together. Locking element 50 is labeled in FIGS. 3C and 4A-B. FIGS. 1A-D show part 52, and FIGS. 2A-D show part 54. Parts 52 and 54 are lockably couplable to each other, and helical elements 22 and 24 are lockably couplable to each other by parts 52 and 54 of locking element 50 being coupled to the helical elements, and being lockably couplable to each other.

For some applications, parts 52 and 54 are generally irreversibly couplable to each other. For some applications, parts 52 and 54 are reversibly couplable to each other.

For some applications, one of the parts of locking element 50 is shaped to define one or more slots 56, and the other part of the locking element comprises one or more tabs 58, each tab being disposable in a respective slot. FIGS. 1A-4B show part 52 being shaped to define slots 56, and part 54 comprising tabs 58. For some applications, both parts of the locking element are shaped to define one or more slots 56 and/or comprise one or more tabs 58.

Typically, tabs 58 are configured to (1) generally allow movement thereof into slots 56, and (2) generally inhibit movement thereof out of the slots. For example, tabs 58 may be (1) disposed circumferentially around part 54, (2) configured to move radially inward when pushed into the part 52, and (3) configured to move radially outward when the tabs reach slots 56. FIGS. 1A-4B show slots 56 exposed on the outer surface of part 52, and, when the two parts of locking element 50 are coupled to each other, tabs 58 protruding through the slots and exposed from the outer surface of part 52. For some applications, the outer surface of locking element 50 (e.g., the outer surface of part 52 thereof) is smooth and/or flush with the surface of the shafts of the helical elements. For example, slots 56 may be not exposed on the outer surface of part 52, and tabs 58 may protrude into, but not through, the slots.

Figure 1A:
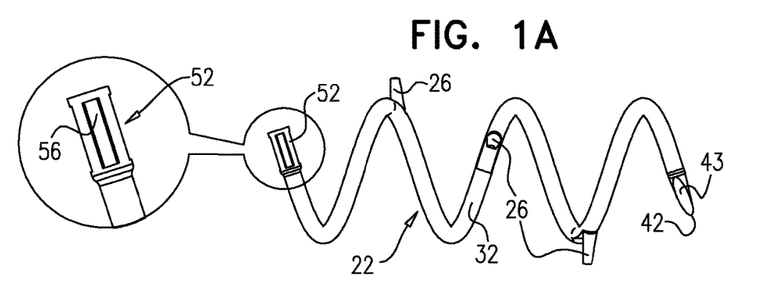
FIGS. 1A-D are schematic illustrations of a first helical element, couplable to a second helical element, for repairing a tendon, in accordance with some applications of the invention.
Figure 1B:
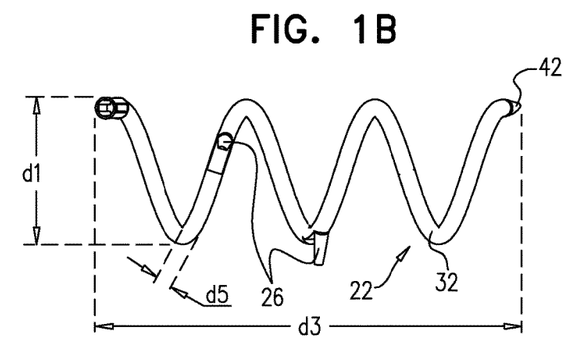
Figure 1C:
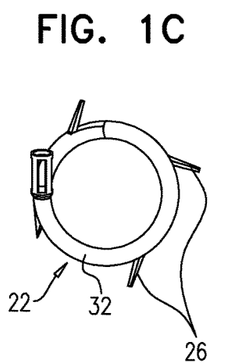
Figure 1D:
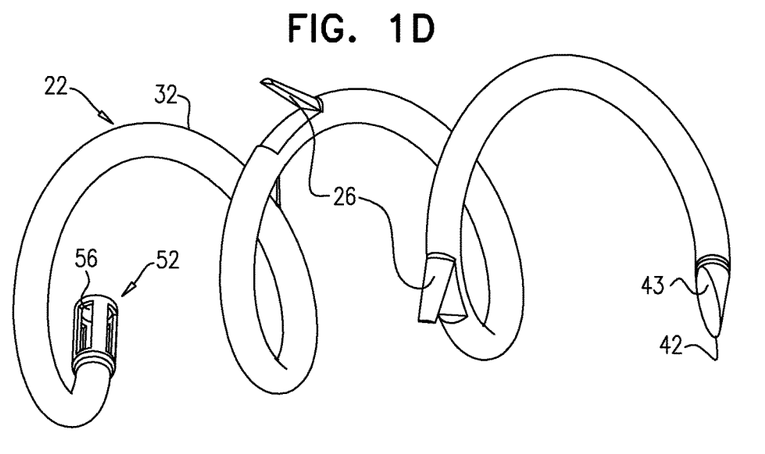
Figure 2A:
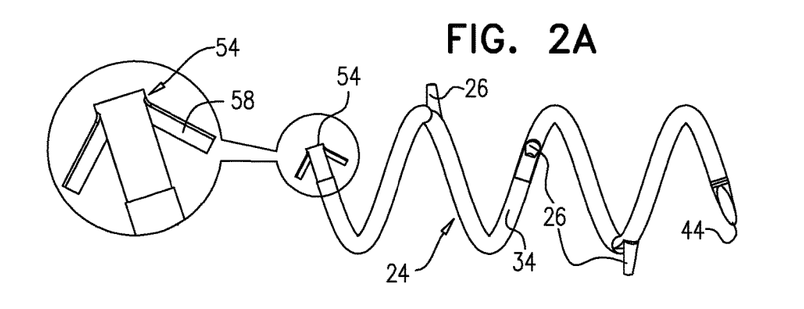
FIGS. 2A-D are schematic illustrations of the second helical element, couplable to the first helical element, for repairing the tendon, in accordance with some applications of the invention.
Figure 2B:
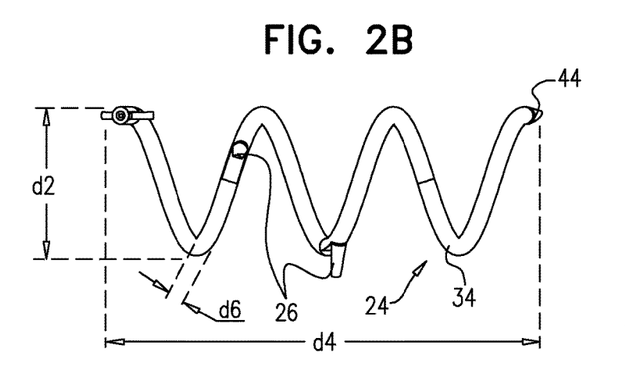
Figure 2C:
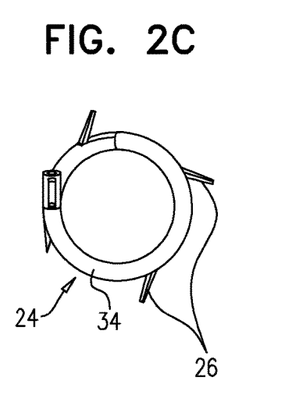
Figure 2D:
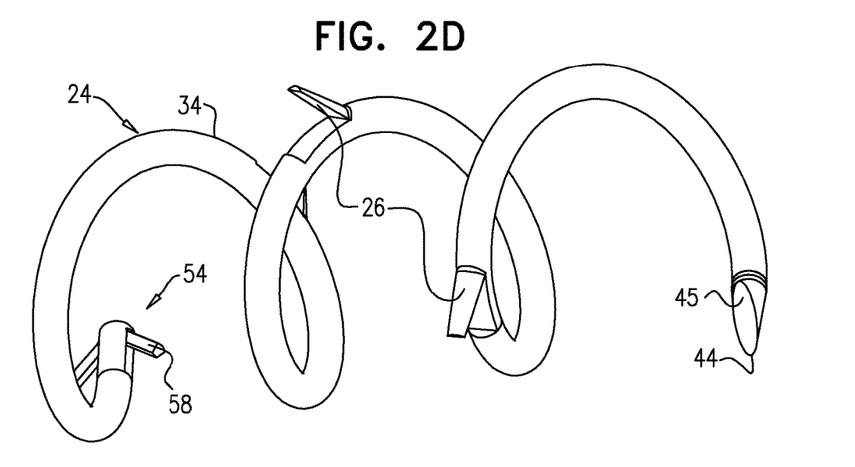
Figure 3A:
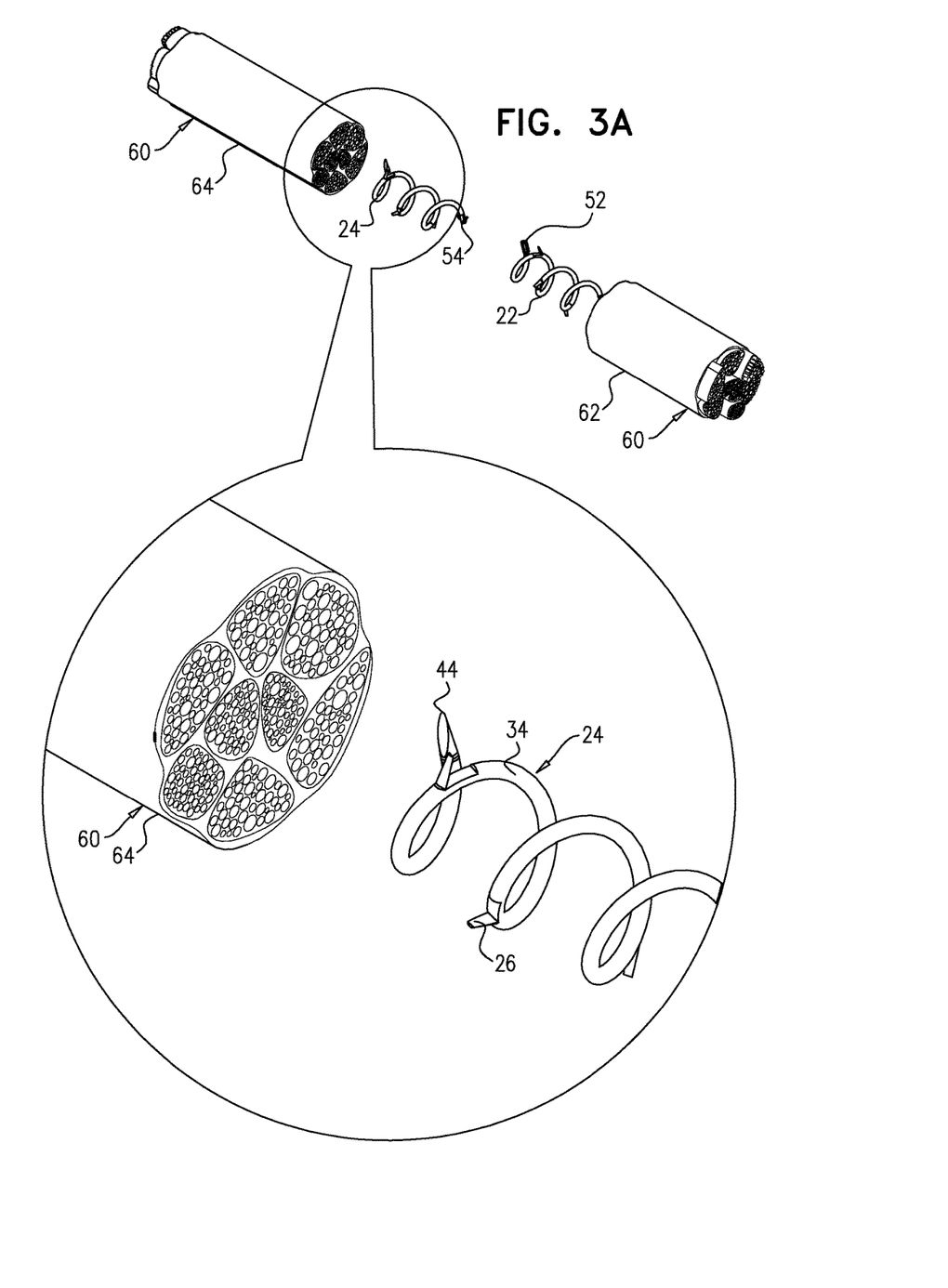
FIGS. 3A-C are schematic illustrations of apparatus, comprising the first and second helical elements, being used to repair the tendon, in accordance with some applications of the invention.
Figure 3B:
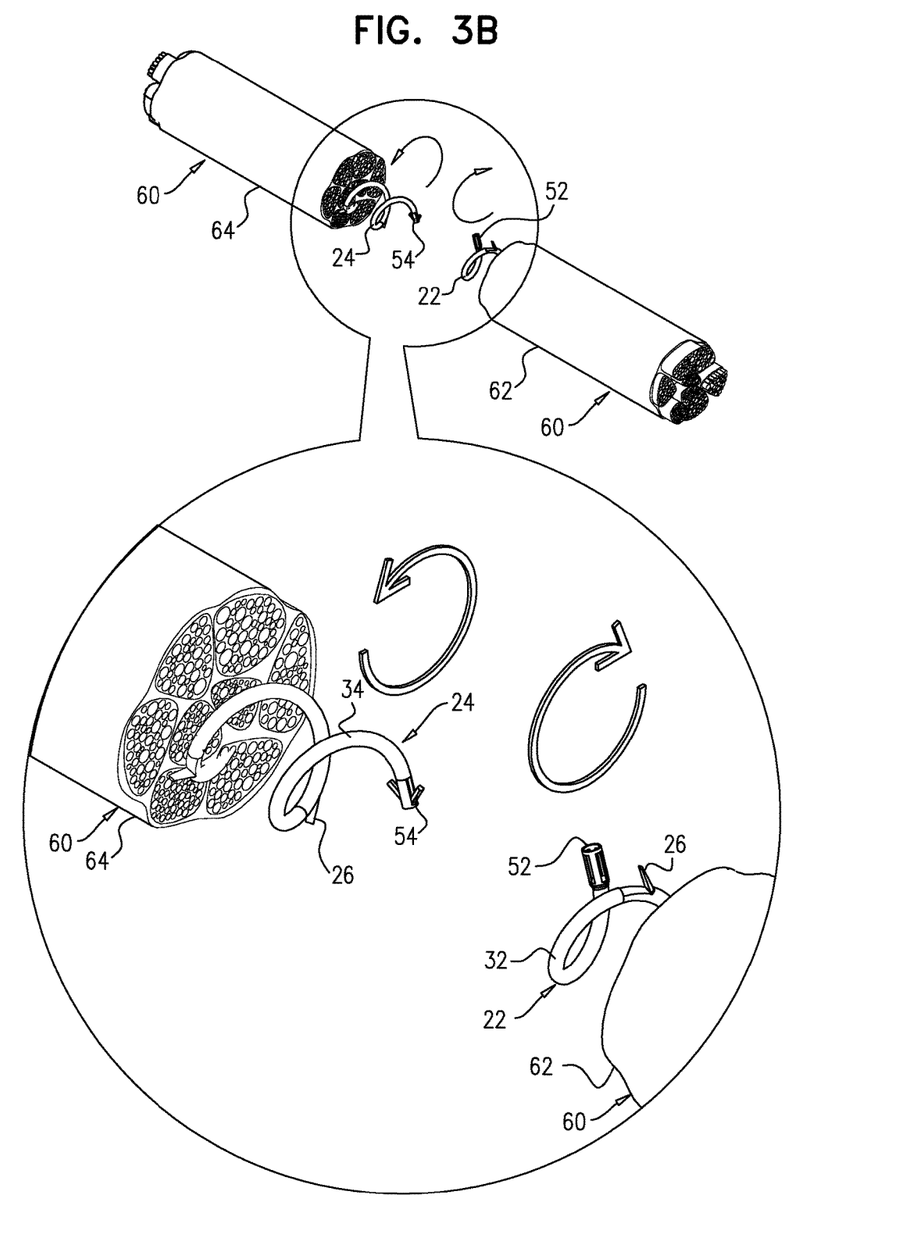
Figure 3C:
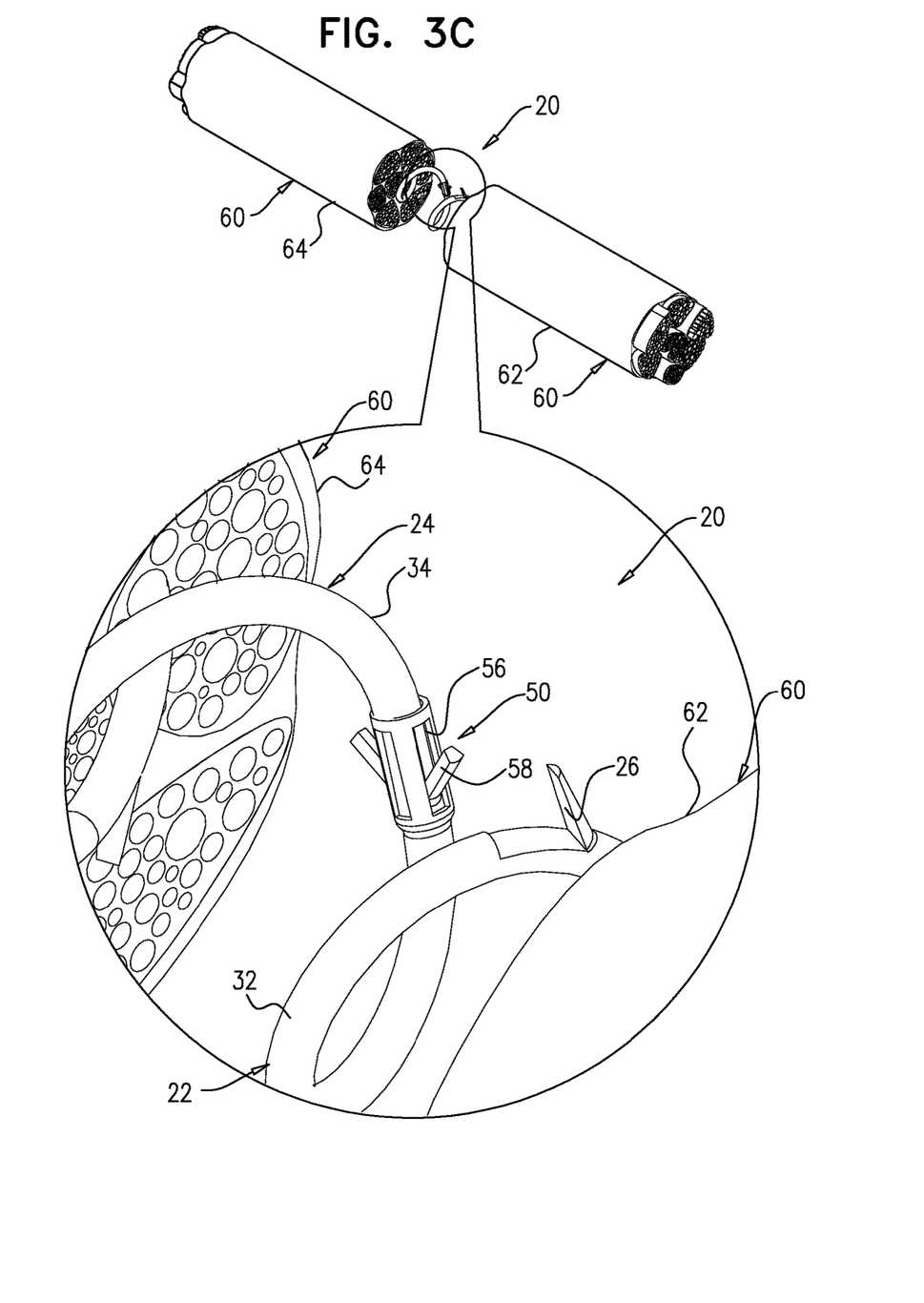

Reference is made to FIGS. 3A-C, which are schematic illustrations of apparatus 20, being used to repair a tendon 60 that has been previously transected into a first portion 62 and a second portion 64 (e.g., in an injury), each portion having an exposed end at the point of transection. FIG. 3A shows helical elements 22 and 24 positioned for coupling to portions 62 and 64 of the tendon, respectively.

FIG. 3B shows helical elements 22 and 24 being coupled to portions 62 and 64 of the tendon, respectively, by being screwed into the portions of the tendon. The cutting edge at the distal end of each helical element facilitates penetration of the tissue (i.e., the tendon).

Typically, the helical elements are screwed into the portions of the tendon via the exposed ends of the portions of the tendon. Typically, the helical elements are screwed into the portions such that the helical elements do not exit the lateral surface of the tendon and/or do not penetrate the surrounding structure of the tendon (e.g., fibrous or synovial sheaths, epitenon, paratenon, and/or tendon bursae). It is hypothesized that such positioning facilitates normal movement (e.g., sliding) of the tendon with respect to the surrounding structure.

FIG. 3C shows helical elements 22 and 24 of apparatus 20 having been lockably coupled to each other, subsequent to their coupling to (e.g., screwing into) the respective portions of tendon 60. Typically, and as shown in FIG. 3C, the helical elements are coupled to each other such that they are disposed collinearly with each other. For some applications, and as shown in FIG. 3C, the helical elements are configured such that, when the helical elements are coupled to each other, they form a continuous helix.

For applications in which apparatus 20 comprises locking element 50, helical elements 22 and 24 are lockably couplable to each other by parts 52 and 54 of locking element 50 being coupled to the helical elements, and lockably couplable to each other. As shown in FIG. 3C, for applications in which one of the parts of locking element 50 is shaped to define one or more slots 56, and the other part of the locking element comprises one or more tabs 58, when the tabs reach respective slots, the tabs move radially outward into the slots, thereby lockably coupling the helical elements to each other.

It is to be noted that locking element 50 typically does not comprise suture (e.g., thread, wire, or similar), and thereby repair of tendon 60 using apparatus 20 is typically performed without the use of suture (except for the closure of a surgical access incision). Alternatively, the parts of locking element 50 may be configured to be coupled to each other using suture. Additionally, the parts may be configured to be brought together using the suture, e.g., by slidably coupling the suture to at least one of the parts and tightening the suture.

Figure 4A:
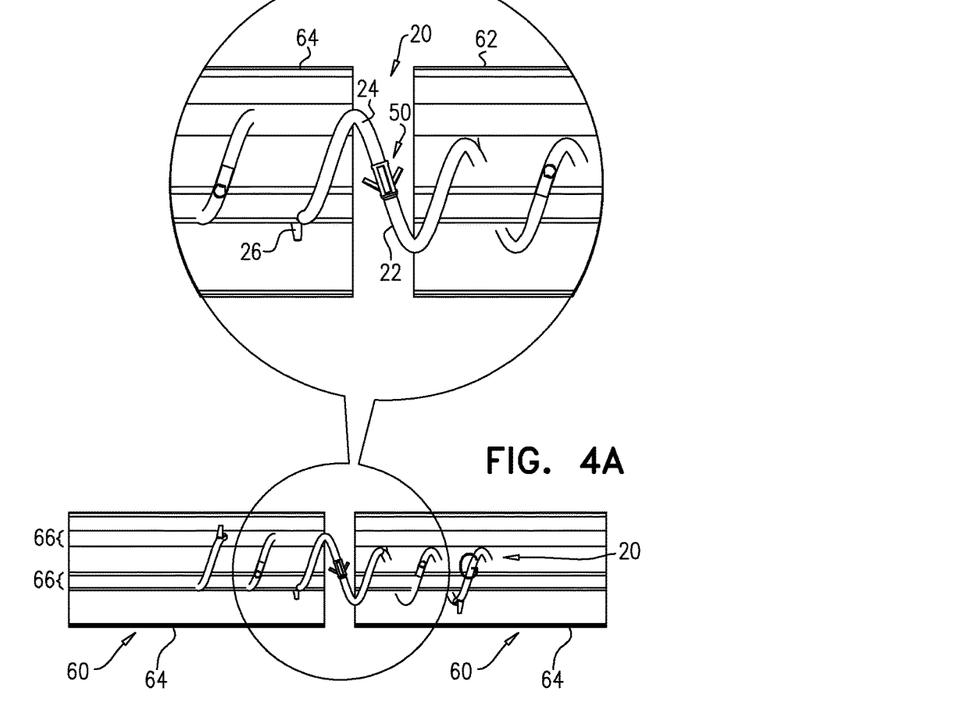
FIGS. 4A-B are schematic illustrations of the apparatus, comprising the first and second helical elements, having been used to repair the tendon, in accordance with some applications of the invention.
Figure 4B:
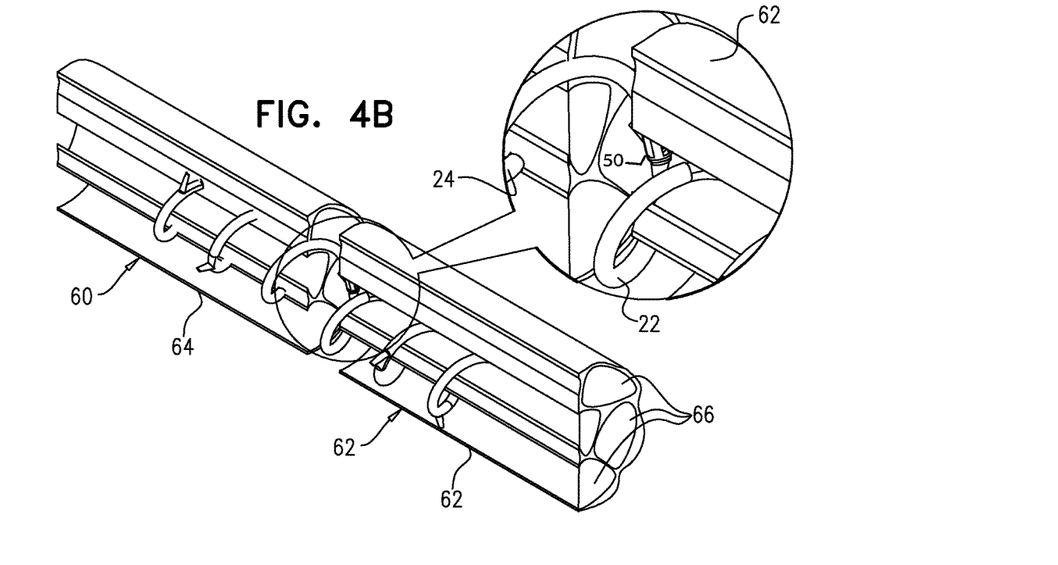

Reference is made to FIGS. 4A-B, which are schematic illustrations of apparatus 20, coupling the two portions of transected tendon 60 to each other, in accordance with some applications of the invention. FIG. 4A is a two-dimensional cutaway, and FIG. 4B is a three-dimensional cutaway. As described hereinabove, helical elements 22 and 24 are typically screwed into the portions of the tendon via the exposed ends of the portions. Also as described hereinabove, the helical elements typically do not exit the lateral surface of the tendon.

As shown in FIGS. 4A-B, each helical element is typically screwed into a respective portion of the tendon such that the shaft of the helical element is coiled around one or more fiber bundles (e.g., fascicles and subfascicles), and/or penetrates one or more of the fiber bundles. It is hypothesized that this arrangement of the helical elements within the tendon increases contact between the helical elements and structures of the tendon, thereby increasing the strength of the coupling of the helical elements to the tendon portions and, thereby, increasing the strength of the coupling of the tendon portions to each other. It is further hypothesized that this increased strength of coupling reduces slipping of the helical elements within the tendon portions, and thereby inhibits any increase in a distance between the tendon portions following coupling of the two helical elements to each other.

Reference is again made to FIGS. 3C-4B. For clarity, FIGS. 3C-4B show a gap between portions 62 and 64 of tendon 60, and show parts 52 and 54 of locking element 50 protruding from the exposed ends of the tendon. However, typically, the helical elements are screwed into the tendon such that little or none of the helical elements and/or the parts of the locking element protrude from the exposed ends. Typically, the tendon (e.g., the portions thereof) are sufficiently soft and/or pliable that the exposed ends may be temporarily squashed together during the coupling of the two parts of locking element 50, thereby facilitating this coupling even when little or none of the parts of the locking element are exposed from the exposed ends of the tendon.

FIGS. 3A-4B show apparatus 20 being used to couple two portions of a tendon, so as to repair the tendon. However, it is to be noted that the scope of the present invention includes the use of apparatus 20 to couple other tissues. In particular, the scope of the present invention includes the use of apparatus 20 to repair other transected elongate and/or tubular tissues, such as a transected blood vessel, ureter, or urethra.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for use with at least one tissue of a subject, the apparatus comprising:
   a first helical element, configured to be coupled to a first portion of the tissue of the subject;
   a second helical element, configured to be coupled to a second portion of the tissue of the subject; and
   a locking element including two parts, a first said part at an end of said first helical element and shaped to define at least one slot, a second said part at an end of said second helical element and shaped to define at least one respective tab, said locking element configured, following the coupling of the first and second helical elements to the first and second portions of the tissue, to couple the first helical element to the second helical element by said at least one tab being disposed in said at least one slot, such that the first and second helical elements are collinear.

2. The apparatus according to claim 1, wherein the locking element is configured to lockably couple the first helical element to the second helical element.

3. The apparatus according to claim 1, wherein no portion of the locking element comprises suture.

4. The apparatus according to claim 1, wherein the two helical elements are shaped to have the same handedness.

5. The apparatus according to claim 1, wherein the apparatus is configured to inhibit an increase in a distance between the first and second portions of the tissue when (1) the first helical element is coupled to the first portion of the tissue, and (2) when the second helical element is coupled to the second portion of the tissue and is lockably coupled by the locking element to the first helical element.

6. The apparatus according to claim 1, wherein said locking element is configured to couple said first helical element to said second helical element such that said first and second helical elements form a continuous helix.

7. The apparatus according to claim 1, wherein said first and second helical elements include at least one of:
   (a) shafts having cross-sectional diameters selected according to the at least one tissue; and
   (b) shafts having helical pitches configured according to the at least one tissue.

8. The apparatus according to claim 1, wherein:
   the first portion of the tissue of the subject includes a first portion of a damaged tissue of the subject,
   the second portion of the tissue of the subject includes a second portion of the damaged tissue of the subject, and
   the apparatus is configured to facilitate repair of the damaged tissue of the subject.

9. The apparatus according to claim 8, wherein:
   the damaged tissue includes one of a transected blood vessel, a transected ureter, a transected urethra, and a transected tendon of the subject, and
   the apparatus is configured to facilitate repair of the damaged tissue by being configured to inhibit an increase in a distance between first and second portions of the damaged tissue.

10. The apparatus according to claim 8, wherein the damaged tissue includes a transected tendon of the subject, and wherein the helical elements are configured to be screwed into respective exposed ends of the first and second portions of the transected tendon at the points of transection.

11. The apparatus according to claim 8, wherein the damaged tissue includes a transected tendon of the subject, and wherein the helical elements are configured to not penetrate an epitenon of the tendon of the subject.

12. The apparatus according to claim 1, wherein each of said first and second helical elements includes at least one projection configured to allow said helical element to be screwed into the at least one tissue in a first direction and configured to inhibit movement of said helical elements in a second direction out of the at least one tissue.

13. The apparatus according to claim 12, wherein each of said at least one projection comprises a continuous piece of material formed from one of said first and second helical elements.

14. The apparatus according to claim 12, wherein each of said at least one projection comprises a discrete piece of material coupled to one of said first and second helical elements.

15. The apparatus according to claim 1, wherein:
each helical element has a distal end and a proximal end, the distal end of each helical element is configured to be coupled to the tissue of the subject, and
each part of the locking element being coupled to a proximal end of a respective helical element, and the parts of the locking element being lockably coupleable to each other.

16. The apparatus according to claim 15, wherein the distal end of each helical element is shaped to define a cutting edge that is asymmetrically tapered.

17. The apparatus according to claim 15, the parts of the locking element being coupleable to each other by the at least one tab being disposed in the at least one slot.

18. The apparatus according to claim 17, wherein said locking element parts are lockably coupleable to each other, and wherein each of said at least one tab is configured to inhibit movement thereof out of said respective slot.

19. The apparatus according to claim 17, wherein said parts of said locking element are configured to be coupleable at multiple relative rotational positions of said helical elements.

20. A method for using an apparatus with at least one tissue of a subject, the method comprising:
coupling a first helical element to a first portion of the tissue of the subject;
coupling a second helical element to a second portion of the tissue of the subject; and
subsequently, lockably coupling the first helical to the second helical element with a locking element including two parts, a first said part at an end of said first helical element and shaped to define at least one slot and a second said part at an end of said second helical element and shaped to define at least one respective tab, said at least one tab being disposed in said at least one slot, such that the first and second helical elements are collinear.

21. The method according to claim 20, further comprising, subsequent to coupling the helical elements to the portions of the tissue of the subject, and prior to coupling the first helical element to the second helical element, at least one of enabling full contact and reducing a distance between the first and second portions of the tissue of the subject.

22. The method according to claim 20, wherein said coupling a first helical element to a first portion of the tissue of the subject includes directing said first helical element in a first direction along the first portion of the tissue away from a point of transection; and
wherein said coupling a second helical element to a second portion of the tissue of the subject includes directing said second helical element in a second direction along the second portion of the tissue away from a point of transection.

23. The method according to claim 20, wherein said method includes increasing contact between said helical elements and structures of the at least one tissue, thereby increasing a strength of the coupling of the helical elements to the first and second portions of the tissue and, thereby, increasing a strength of the coupling of the first and second tissue portions to each other.

24. The method according to claim 20, wherein said lockably coupling includes inserting a portion of a locking member coupled to one helical element into a portion of the locking member coupled to the other helical element, thereby reducing a distance between the first and second helical elements.

* * * * *